United States Patent
Cho et al.

(10) Patent No.: US 9,532,762 B2
(45) Date of Patent: Jan. 3, 2017

(54) APPARATUS AND METHOD FOR LESION DETECTION

(71) Applicant: Samsung Electronics Co., Ltd., Suwon-si (KR)

(72) Inventors: Baek Hwan Cho, Seoul (KR); Yeong Kyeong Seong, Yongin-si (KR); Ye Hoon Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/495,545

(22) Filed: Sep. 24, 2014

(65) Prior Publication Data

US 2015/0230773 A1  Aug. 20, 2015

(30) Foreign Application Priority Data

Feb. 19, 2014  (KR) ........................ 10-2014-0019265

(51) Int. Cl.
| | |
|---|---|
| *G06K 9/00* | (2006.01) |
| *A61B 6/00* | (2006.01) |
| *G06K 9/62* | (2006.01) |
| *A61B 8/08* | (2006.01) |

(52) U.S. Cl.
CPC ............. *A61B 6/5217* (2013.01); *A61B 6/502* (2013.01); *A61B 8/0825* (2013.01); *A61B 8/5223* (2013.01); *G06K 9/6217* (2013.01)

(58) Field of Classification Search
None
See application file for complete search history.

(56) References Cited

U.S. PATENT DOCUMENTS

| | | | |
|---|---|---|---|
| 7,092,749 B2 | 8/2006 | Fowkes et al. | |
| 7,466,848 B2 * | 12/2008 | Metaxas | ............... A61B 5/055 382/128 |
| 7,640,051 B2 | 12/2009 | Krishnan et al. | |
| 7,648,460 B2 | 1/2010 | Simopoulos et al. | |
| 7,865,002 B2 * | 1/2011 | Basilico | ............... G06T 7/0012 378/37 |
| 8,050,734 B2 | 11/2011 | Miller et al. | |

(Continued)

FOREIGN PATENT DOCUMENTS

| | | |
|---|---|---|
| JP | 2011-110429 A | 6/2011 |
| JP | 2012-192159 A | 10/2012 |
| JP | 2012-235934 A | 12/2012 |
| KR | 10-2013-0012297 A | 2/2013 |

OTHER PUBLICATIONS

Hinton, Geoffrey E., et al. "Reducing the dimensionality of data with neural networks." Science 313.5786 (2006): 504-507.

(Continued)

*Primary Examiner* — Soo Jin Park
(74) *Attorney, Agent, or Firm* — Jefferson IP Law, LLP

(57) ABSTRACT

An apparatus and a method for lesion detection are provided. The method of lesion detection involves detecting lesion candidates from a medical image, detecting anatomical objects from the medical image, verifying each of the lesion candidate based on anatomical context information comprising information regarding a location relationship between the lesion candidates and the anatomical objects, and removing one or more false positive lesion candidate from the detected lesion candidates based on a verification result.

27 Claims, 13 Drawing Sheets

(56) References Cited

U.S. PATENT DOCUMENTS

| | | |
|---|---|---|
| 8,051,386 B2 | 11/2011 | Rosander et al. |
| 8,064,677 B2 | 11/2011 | Nie et al. |
| 8,160,341 B2 | 4/2012 | Peng et al. |
| 8,218,879 B2 | 7/2012 | Yu et al. |
| 8,369,927 B2 | 2/2013 | Netsch et al. |
| 2005/0207630 A1 | 9/2005 | Chan et al. |
| 2006/0008143 A1 | 1/2006 | Truyen et al. |
| 2008/0107321 A1 | 5/2008 | Oh |
| 2009/0097730 A1* | 4/2009 | Kasai .................. A61B 6/00 382/132 |
| 2009/0103797 A1 | 4/2009 | Hong et al. |
| 2010/0158332 A1* | 6/2010 | Rico .................. A61B 5/4312 382/128 |
| 2011/0026791 A1* | 2/2011 | Collins .................. G06K 9/62 382/131 |
| 2012/0226141 A1 | 9/2012 | Shinoda et al. |
| 2013/0030278 A1 | 1/2013 | Seong et al. |

OTHER PUBLICATIONS

Zeiler, Matthew D., et al. "Adaptive deconvolutional networks for mid and high level feature learning." Computer Vision (ICCV), 2011 IEEE International Conference on. IEEE, 2011 (8 pages).

Jamieson, Andrew R., et al. "Breast image feature learning with adaptive deconvolutional networks." SPIE Medical Imaging. International Society for Optics and Photonics, 2012 (13 pages).

European Search Report issued on Aug. 24, 2015 in counterpart European Application No. 14189610.0 (8 pages, in English).

Vignati, Anna, et al. "A fully automatic lesion detection method for DCE-MRI fat-suppressed breast images." *SPIE Medical Imaging*. International Society for Optics and Photonics, 2009, Lake Buena Vista, FL, USA. (12 pages, in English).

Wang, Shijun, and Ronald M. Summers. "Machine learning and radiology." *Medical image analysis* 16.5 (2012): 933-951, Bethesda, MD, USA. (20 pages, in English).

\* cited by examiner

APPARATUS AND METHOD FOR LESION DETECTION

CROSS-REFERENCE TO RELATED APPLICATION(S)

This application claims the benefit under 35 USC 119(a) of Korean Patent Application No. 10-2014-0019265 filed on Feb. 19, 2014, in the Korean Intellectual Property Office, the entire disclosure of which is incorporated herein by reference for all purposes.

BACKGROUND

1. Field

The following description relates to a technique of detecting lesion from a medical image, and to a method and an apparatus for eliminating one or more lesion candidate detected from a medical image as a false positive lesion candidate.

2. Description of Related Art

Computer-Aided Detection (CADe), also called Computer-Aided Diagnosis (CADx), is a technique of automatically detecting lesions from a medical image using a computer for the purpose of assisting a doctor in making a diagnosis. However, the low-resolution of many medical images and the wide-range atypical characteristics of lesions within medical images make it challenging to achieve high accuracy in CAD.

For example, ultrasound images are obtained from a probe whose location and angle are arbitrarily determined by a doctor. Thus, the obtained ultrasound images may contain an atypical image of a lesion due to the different locations and angles of a probe used to obtain the image. Thus, if an algorithm of automatically detecting lesions is applied to such an atypical image, the computer is likely to detect not just lesions but also anatomical objects found in the image as lesions.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for lesion detection includes a lesion candidate detector configured to detect lesion candidates from a medical image, an adjacent object detector configured to detect anatomical objects from the medical image, a lesion candidate verifier configured to verify each of the lesion candidates based on anatomical context information comprising information regarding a location relationship between each of the lesion candidates and the anatomical objects, and a candidate remover configured to remove one or more false positive lesion candidate from among the detected lesion candidates based on a verification result of the lesion candidate verifier.

The apparatus may further include an image receiver configured to obtain the medical image, in which the medical image is an image of a human breast captured using ultrasound waves or X-rays; the adjacent object detector is configured to detect at least one of skin, fat, glandular tissue, muscle, and bone from the breast image as an anatomical object; and the lesion candidate verifier is configured to verify each of the lesion candidates based on anatomical context information comprising information regarding a location relationship between each of the lesion candidates and the at least one of skin, fat, glandular tissue, muscle, and bone.

The lesion candidate detector may be configured to detect the lesion candidates from the medical image using at least one of Haar feature detection technique, deformable part model (DPM), and deep learning technique.

The adjacent object detector may include a plurality of individual object detectors, each of which may detect the anatomical objects individually from the medical image.

Each of the plurality of individual object detectors may be configured to use deep learning technique, sliding window technique, or superpixel technique.

The adjacent object detector may include a single object detector configured to simultaneously detect the anatomical objects from the medical image.

The single object detector may be configured to use deep learning technique, sliding window technique, or superpixel technique.

The single object detector may be configured to extract a plurality of feature maps from the whole medical image or a part of the medical image, allocate the extracted feature maps with corresponding anatomical objects, and label a location of a feature map allocated with a specific anatomical object in the medical image as the specific anatomical object.

The lesion candidate verifier may be configured to use at least one of Support Vector Machine (SVM), Artificial Neural Network (ANN), deep learning technique, and Bayesian Network.

The anatomical context information may include domain knowledge of the anatomical objects and domain knowledge of the lesion candidates, the domain knowledge of the anatomical objects comprising at least one of: "a specific part of a human body has predefined anatomical objects", "different anatomical objects have a predefined location relationship in a specific part of a human body" and "the identical anatomical objects are gathered", and the domain knowledge of the lesion candidate comprising "a specific lesion candidate exists only in specific anatomical objects of a specific part of a human body."

The anatomical context information may include self information that is extracted from the detected lesion candidate and the detected anatomical object, and the self information may include at least one of confidence level information, brightness information, texture information, and shape information.

The anatomical context information may include relationship information that is extracted from a correlation between each of the lesion candidates and each of the anatomical object.

The relationship information may include at least one of a distance between each of the lesion candidates and each of the anatomical objects, a location of each of the lesion candidates relative to each of the anatomical objects, and information on similarity between each of the lesion candidates and each of the anatomical objects in terms of brightness, texture, or shape.

The anatomical context information may include a probability distribution of existence of each of the lesion candidates in the medical image, the probability distribution being obtained from a pre-established learning data.

In response to the medical image being one of 2D continuous frames or one of 3D cross-sectional images, the anatomical context information further may include adjacent image information obtained from an adjacent frame or cross-section, which comprises location information of each of the lesion candidates and each of the anatomical objects.

In another general aspect, a method of lesion detection involves detecting lesion candidates from a medical image, detecting anatomical objects from the medical image, verifying each of the lesion candidate based on anatomical context information comprising information regarding a location relationship between the lesion candidates and the anatomical objects, and removing one or more false positive lesion candidate from the detected lesion candidates based on a verification result.

The general aspect of the method may further involve obtaining the medical image from a medical imaging apparatus, in which the medical image is an image of a breast of a human body captured using ultrasound waves or X-rays, the detecting of anatomical objects comprises detecting at least one of skin, fat, glandular tissue, muscle, and bone from the breast image as an anatomical object, and the verifying of each of the lesion candidates comprises verifying each of the lesion candidates based on anatomical context information comprising information regarding a location relationship between the lesion candidates and the at least one of skin, fat, glandular tissue, muscle, and bone.

The detecting of lesion candidates may involve detecting the lesion candidates from the medical image using at least one of Haar feature detection technique, deformable part model (DPM), and deep learning technique.

The detecting of the anatomical objects may involve detecting a plurality of individual objects to detect the anatomical objects from the medical image individually.

The detecting of each of the plurality of individual objects may utilize deep learning technique, sliding window technique, or superpixel technique.

The detecting of the anatomical objects may involve detecting all of the anatomical objects from the medical image simultaneously.

The simultaneous detecting of all of the anatomical objects from the medical image may utilize deep learning technique, sliding window technique, or superpixel technique.

The simultaneous detecting of all of the anatomical objects may involve: extracting a plurality of feature maps from the whole medical image or a part of the medical image, allocating each of the plurality of extracted feature maps with corresponding anatomical objects, and labeling a location of a feature map allocated with a specific anatomical object in the medical image with the specific anatomical object.

The verifying of each of the lesion candidates may utilize at least one of Support Vector Machine (SVM), Artificial Neural Network (ANN) and Bayesian Network.

The anatomical context information may include domain knowledge of the anatomical objects and domain knowledge of the lesion candidates, and the domain knowledge of the anatomical objects may include at least one of: "a specific part of a human body has predefined anatomical objects", "different anatomical objects have a predefined location relationship in a specific part of a human body" and "the identical anatomical objects are gathered", and the domain knowledge of the lesion candidate may include "a specific lesion candidate exists only in specific anatomical objects of a specific part of a human body."

The anatomical context information may include self information that is respectively extracted from the lesion candidates and the anatomical objects, and the self information may include at least one of confidence level information, brightness information, texture information, and shape information.

The anatomical context information may include relationship information that is extracted from a correlation between each of the lesion candidates and each of the anatomical objects. The relationship information may include at least one of a distance between each of the lesion candidates and each of the anatomical objects, a location of each of the lesion candidates relative to each of the anatomical objects, and information on similarity between each of the lesion candidates and each of the anatomical objects in terms of brightness, texture, or shape.

The anatomical context information may include a probability distribution of existence of each of the lesion candidates in the medical image, the probability distribution being obtained from pre-established learning data.

In response to the medical image being one of two-dimensional (2D) continuous frames or one of three-dimensional (3D) cross-sectional image, the anatomical context information may further include adjacent image information from an adjacent frame or an adjacent cross-section, which includes location information of each of the lesion candidates or each of the anatomical objects.

In another general aspect, an apparatus for lesion detection includes a memory configured to store a medical image, and a processor configured to detect lesion candidates and anatomical objects from the medical image, configured to verify each of the detected lesion candidates based on anatomical context information comprising information regarding a location relationship between each of the lesion candidates and the detected anatomical objects, and configured to remove one or more false positive lesion candidates from among the detected lesion candidates based on a verification result.

The general aspect of the apparatus may further include an image receiver configured to obtain the medical image from a medical imaging apparatus and to store the medical image in the memory, the medical image being an image of a human breast captured using ultrasound waves or X-rays, and the anatomical objects comprising at least one of skin, fat, glandular tissue, muscle, and bone from the breast image. The general aspect of the apparatus may further include a display screen configured to output a view of the medical image in which the lesion candidates remaining after the removing of the one or more false positive lesion candidates are displayed.

Other features and aspects will be apparent from the following detailed description, the drawings, and the claims.

Figure 1:
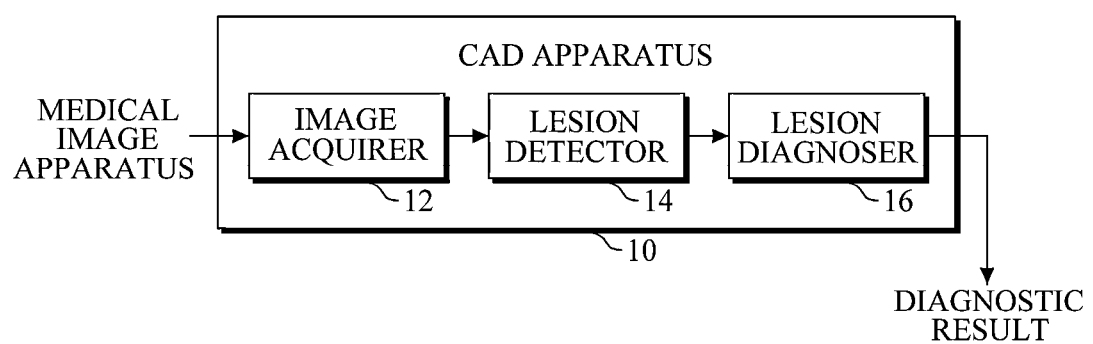
FIG. 1 is a block diagram illustrating a configuration of a Computer-Aided Diagnosis (CAD) apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

According to an example of an apparatus and/or a method for removing one or more false positive lesion candidates from a medical image, a technology of detecting one or more lesion candidates in a Computer-Aided Detection (CADe) or Computer-Aided Diagnosis (CADx) is provided. The technology may be used when detecting a lesion candidate from an ultrasound image or X-ray breast medical image. For example, the technology may be used with breast ultrasound image.

In the present disclosure, the term "anatomical object" may refer to an element that is distinguishable by a specific anatomical characteristic or function. For example, a breast may a variety of tissues and components, including skin, subcutaneous fat, glandular tissue, retromammary fat, pectoralis muscle and ribs, as anatomical objects.

The term "lesion candidate region/portion" refers to a specific region detected by CAD that is likely to be diagnosed as a lesion. A doctor determines whether or not a lesion candidate region detected by CAD is a true lesion in order to diagnose a patient.

The apparatus and method for removing one or more false positive lesion candidate regions in a medical image entails verifying lesion candidates, detected from a medical image, using anatomical context information, and then removing any false positive lesion candidate. That is, firstly, lesion candidates and anatomical objects are detected from an image. Then, a location of each detected lesion candidate, a location of each detected anatomical object, and a location relationship between each detected lesion candidate and each detected anatomical object are verified based on anatomical context information. Then, any false positive lesion candidate is removed from the lesion candidates based on the verification result. In this manner, it may become more efficient to detect lesion candidates.

The "false positive lesion candidate" refers to a lesion candidate that is mistakenly detected instead of a lesion that needs to be medically diagnosed. For example, if a specific anatomical object, such as fat, is determined to be a lesion candidate, the lesion candidate is highly likely to be false positive. In another example, if a breast image is captured and a lesion in the breast image is determined to be located in an area where a tumor or a cyst related to breast cancer is usually not found, the lesion candidate is highly likely to be false positive.

If a medical image is an ultrasound or X-ray breast image, a cyst of breast cancer may be identified as a lesion candidate, while skin, subcutaneous fat, glandular tissue, retromammary fat, pectoralis muscle and ribs may be detected as anatomical objects.

A lesion candidate may be detected using various algorithms to automatically detect a lesion candidate from an image. For example, Haar feature detection technique, deformable part model, deep learning technique, or the like may be utilized.

Detecting an anatomical object may be performed by detecting each of a plurality of anatomical objects from an image individually. In this case, a single deep learning technique or various deep learning techniques, such as Convolutional Deep Belief Network (CDBN), Convolutional Neural Network (CNN), or the like, may be utilized. In addition, different detectors may be used for each distinct anatomical object: for example, a skin detector for skin, a fat detector for fat, a glandular tissue detector for a glandular tissue, and a muscle detector for muscle.

Meanwhile, a plurality of anatomical objects may be detected at once from an ultrasound breast image. In such an example, a deep learning technique, a sliding window technique or a superpixel technique may be utilized. For example, various feature maps may be extracted from an ultrasound breast image, the extracted feature maps may be allocated with corresponding anatomical objects, and a location of a feature map allocated with a specific anatomical object in an image may be labeled with the specific anatomical object.

Detected in the above manner, skin, fat, muscle, and bone, and any other anatomical objects, may be verified based on anatomical context information about a location relationship between anatomical objects.

Anatomical context information may include domain knowledge associated with a lesion candidate and relevant anatomical objects. In addition, the anatomical context information may include information on a lesion candidate and information on each anatomical object. Moreover, the anatomical context information may include information about a location relationship between a lesion candidate and an anatomical object. Furthermore, the anatomical context information may include a probability distribution of existence of a lesion candidate and/or anatomical object in a medical image of a specific part of a human body. The probability distribution may be acquired based on pre-established learning data. In an example in which a medical image is one of two-dimensional (2D) continuous video frames or one of three-dimensional (3D) cross-sectional images, the anatomical context information may include adjacent image information obtained from an adjacent frame or an adjacent cross-section, such as location information of an anatomical object.

Hereinafter, examples of apparatuses and methods for detecting lesion by removing a false positive lesion candidate from a medical image are described with reference to drawings.

For example, an apparatus and/or method for removing a false positive lesion candidate from a medical image that is a 2D ultrasound breast image is provided. However, the medical image is not limited to an ultrasound breast image. For example, the medical image may be an ultrasound or X-ray image of a different part of a human body, and the medical image may be a 2D or 3D image.

FIG. 1 is a block diagram illustrating a configuration of a Computer-Aided Diagnosis (CAD) apparatus.

Referring to FIG. 1, the illustrated CAD apparatus 10 includes an image acquirer 12, a lesion detector 14, and a lesion diagnoser 16. A medical image apparatus may capture an ultrasound image of a patient's breast. The image acquirer 12 may then receive an image from the medical image apparatus that stores such a captured image. The lesion detector 14 may determine whether the received image from the image acquirer 12 includes one or more lesion candidate by applying a lesion detection algorithm to the received image, and may detect a location of each detected lesion candidate in the received image. The lesion diagnoser 16 may determine whether the detected lesion candidates are malignant. The CAD apparatus 10 may display the detected lesion candidate within an image along with a diagnostic result.

In such a CAD apparatus, the lesion detector 14 may detect a plurality of false positive lesion candidates as well as a lesion candidate that corresponds to an actual lesion due to poor-definition and atypical ultrasound image. A false positive lesion candidate corresponds to a detection error. Therefore, in order to enhance diagnostic performance and efficiency, the lesion detector 14 has to reduce the number of detection errors, that is, the number of false positive lesion candidates.

Figure 2:
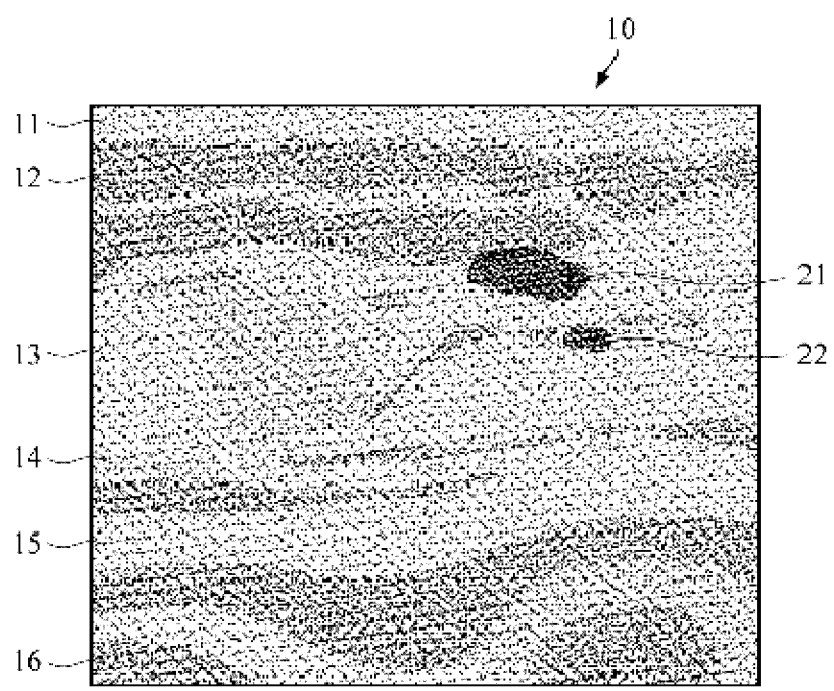
FIG. 2 is a diagram illustrating an example of lesion candidates in a breast ultrasound image and an anatomical structure of the breast ultrasound image.

FIG. 2 illustrates an example of a medical image. The medical image is an ultrasound breast image including examples of lesion candidates disposed among anatomical structures of a human breast.

Referring to FIG. 2, an example of a 2D ultrasound image of a human breast is provided. An image 10 illustrated in FIG. 2 includes anatomical objects, such as skin 11, subcutaneous fat 12, glandular tissue 13, retromammary fat 14, pectoralis muscle 15 and rib 16. In addition, the image 10 includes lesion candidates 21 and 22, such as a cyst and a malignant lesion. Such anatomical objects are anatomically structured in a manner in which the skin 11, the subcutaneous fat 12, the glandular tissue 13, the retromammary fat 14, the pectoralis muscle 15 and the rib 16 are arranged from the surface to the inside in order. In addition, the lesion candidates 21 and 22 may be found in various locations in the image 10.

Figure 3:
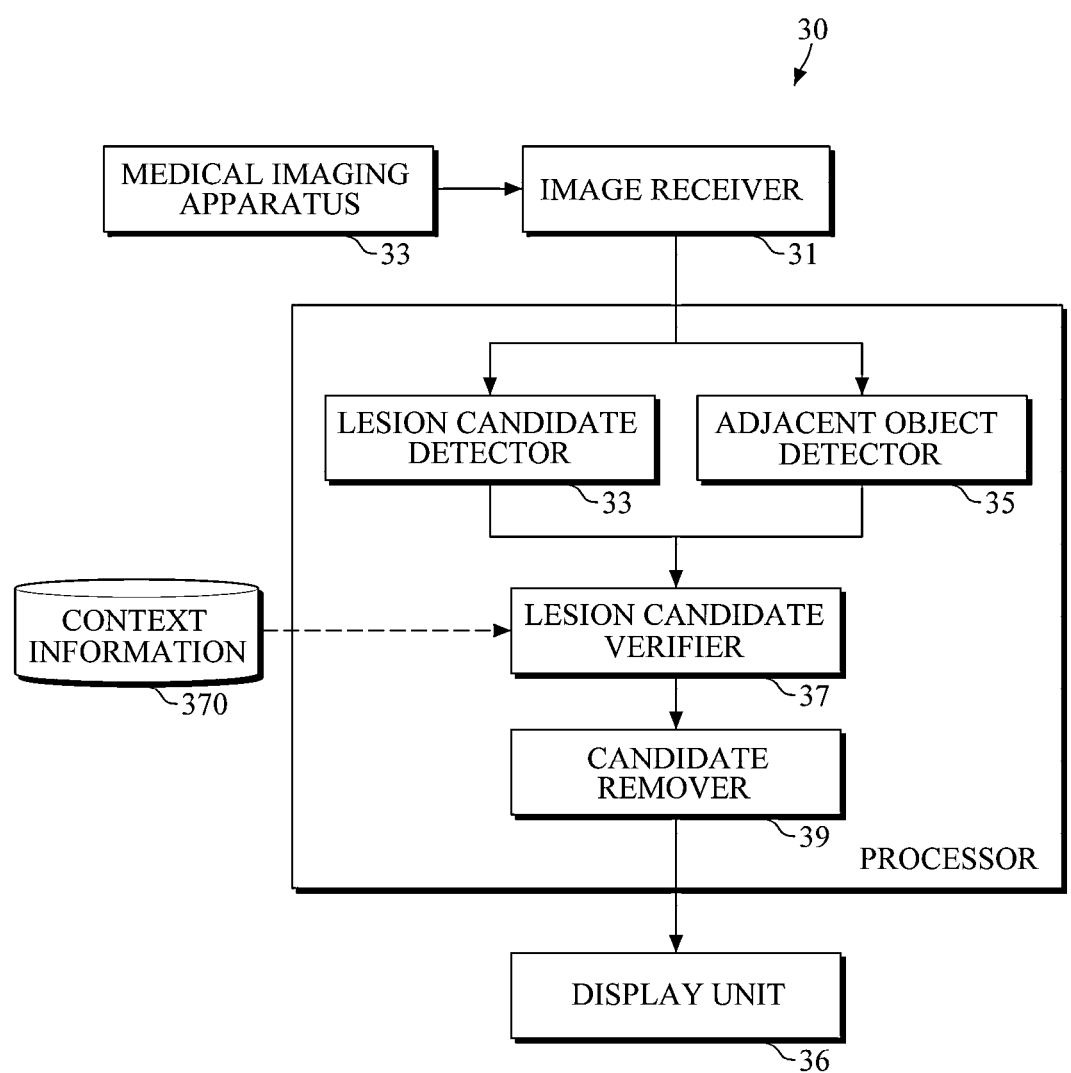
FIG. 3 is a block diagram illustrating an example of an apparatus for removing one or more false positive lesion candidates.

FIG. 3 is a block diagram illustrating an example of an apparatus for detecting lesion by removing a false positive lesion candidate from a medical image.

Referring to FIG. 3, an apparatus 30 for detecting lesion may include components, such as an image receiver 31, a lesion candidate detector 33, an adjacent object detector 35, a lesion candidate verifier 37, and a candidate remover 39, a display unit 36, or the like.

The image receiver 31 is a component that receives a medical image. A medical image may be, for example, an ultrasound image of a human breast that is captured using ultrasonic waves, as shown in FIG. 2. The medical image may be received from a medical image diagnostic/capturing device, from an imaging apparatus that captures a specific part of a human body using ultrasonic waves or X-rays, or from a storage device that stores medical images captured by the medical image diagnostic/capturing device. The medical image diagnostic/capturing device and storage devices may be collectively referred herein as a medical imagining apparatus. According to one example, the image receiver 31 may be implemented as an integral part of such a medical imaging apparatus or may communicate with such a medical imaging apparatus via a wired or a wireless communication. The received image may be stored in a memory of the apparatus 30 for analysis.

The lesion candidate detector 33, the adjacent object detector 35, the lesion candidate verifier 37, and the candidate remover 39 may be implemented on one or more computer processors.

The lesion candidate detector 33 is a component that analyzes a medical image to determine whether the medical image includes one or more lesion candidates and to detect a location of each detected lesion candidate in the medical image. In order to detect a lesion candidate, the lesion candidate detector 33 may use a Haar feature detection technique, a deformable part model technique, a deep learning technique, or the like. The lesion candidate detector 33 may make each detected lesion candidate correspond to a score indicating a confidence level thereof. A confidence level score may be a measurement that represents a possibility that each lesion candidate would be determined to be a true lesion.

The adjacent object detector 35 may detect a plurality of anatomical objects from a medical image. If a medical image is an ultrasound breast image 10, the adjacent object detector 35 may detect skin, fat, glandular tissue, muscle, and bone within the image as anatomical objects. The adjacent object detector 35 may include a single object detector that detects all anatomical objects at once, or may include a plurality of individual object detectors that detect anatomical objects individually. Hereinafter, the adjacent object detector 35 is described in detail with reference to FIGS. 4 to 6.

Based on context information 370, including information associated anatomical context, the lesion candidate verifier 37 may verify a lesion candidate detected by the lesion candidate detector 33 and an anatomical object detected by the adjacent object detector 35. For example, the lesion candidate verifier 37 may use Support Vector Machine (SVM), Artificial Neural Network (ANN), Bayesian Network, or any other machine learning and statistical techniques. The lesion candidate verifier 37 is described in detail with reference to FIG. 8.

The context information 370 may include context information that indicates anatomical context of each anatomical object included in a medical image. The context information may include domain knowledge that generally indicates a location of a lesion candidate, a location of each anatomical object, and a location relationship between each lesion candidate and each anatomical object. For example, if a medical image is the ultrasound breast image 10, the lesion candidate verifier 37 may use domain knowledge that indicates locations of a detected lesion candidate, skin, fat, glandular tissue, muscle, and bones, and a correlation between the locations of the above. The context information 370 may be stored in a computer readable storage medium. The context information 370 is hereinafter described in detail with reference to FIG. 9.

For example, suppose that the lesion candidate detector 33 detects a lesion candidate by analyzing an image using a DPM technique and determining a specific region in the image as a "lesion candidate with a confidence level of 85%", that the adjacent object detector 35 detects an anatomical object by analyzing the image using a sliding window technique and determines another specific region in the image as "subcutaneous fat with a confidence level of 95%", and that that the adjacent object detector 35 detects any other anatomical object, such as "skin", "glandular tissue", "retromammary fat" and "pectoralis muscle" in the same way.

In this example, the lesion candidate verifier 37 may verify whether the detected "lesion candidate" is a true lesion based on anatomical context information. For instance, the lesion candidate verifier 37 may verify a location relationship between a specific region (hereinafter referred to as Region A) detected to be a lesion candidate and each anatomical object. In other words, the lesion candidate verifier 37 may refer to anatomical context information indicating that a location of Region A is located at the same point of, close to, or far from a location of each anatomical object. Accordingly, the lesion candidate verifier 37 may determine whether Region A is a lesion highly likely to be determined to be a true lesion or whether Region A is a lesion less likely to be determined to be a true lesion.

The candidate remover 39 may receive the verification result from the lesion candidate verifier 37. Accordingly, the candidate remover may remove lesion candidates determined to be a false positive candidate by the candidate remover 39 among the lesion candidates detected by the lesion candidate detector 33, and include the remaining lesion candidates in the original image 10 to be displayed. The resultant image 10 is described in detail with reference to FIG. 7.

Figure 4:
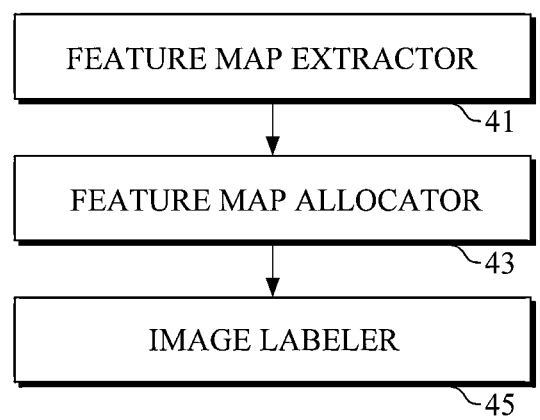
FIG. 4 is a block diagram illustrating an example of an adjacent object detector shown in the example of FIG. 3.

FIG. 4 is a block diagram illustrating an example of an adjacent object detector shown in the apparatus illustrated in FIG. 3.

Referring to FIG. 4, as an example of the adjacent object detector 31 in FIG. 3, a single detector 40 for simultaneously detecting all anatomical objects in an image is provided. In the example illustrated in FIG. 4, the single detector 40 uses the sliding window technique in detecting a plurality of anatomical objects from a medical image.

As illustrated in FIG. 4, the single detector 40 may detect anatomical objects using histogram of gradient (HOG) features, that is, feature maps. To this end, the single detector 40 may include a feature map extractor 41, a feature map allocator 43, and an image labeler 45. The feature map extractor 41 extracts at least one feature map from an image. The feature map allocator 43 allocates the extracted feature map with a corresponding anatomical object. For this process, the extracted feature map may be compared with a plurality of pre-stored feature maps. If the extracted feature map coincides with any one of a plurality of pre-stored feature maps, the feature map allocator 43 may allocate the extracted feature map with an anatomical object corresponding to the coincided feature map. That is, the image labeler 45 may label a location of a feature map allocated with a specific anatomical object in an image with the specific anatomical object. Accordingly, a location of the feature map in the image may be detected as the specific anatomical object.

Alternatively, the single detector 40 may use the superpixel technique. In this case, the single detector may be configured to be a classifier that segments pixels in an image into superpixels and then use image information of features of each superpixel, such as intensity, texture, sparse coding, and a deep belief network of a superpixel.

Figure 5:
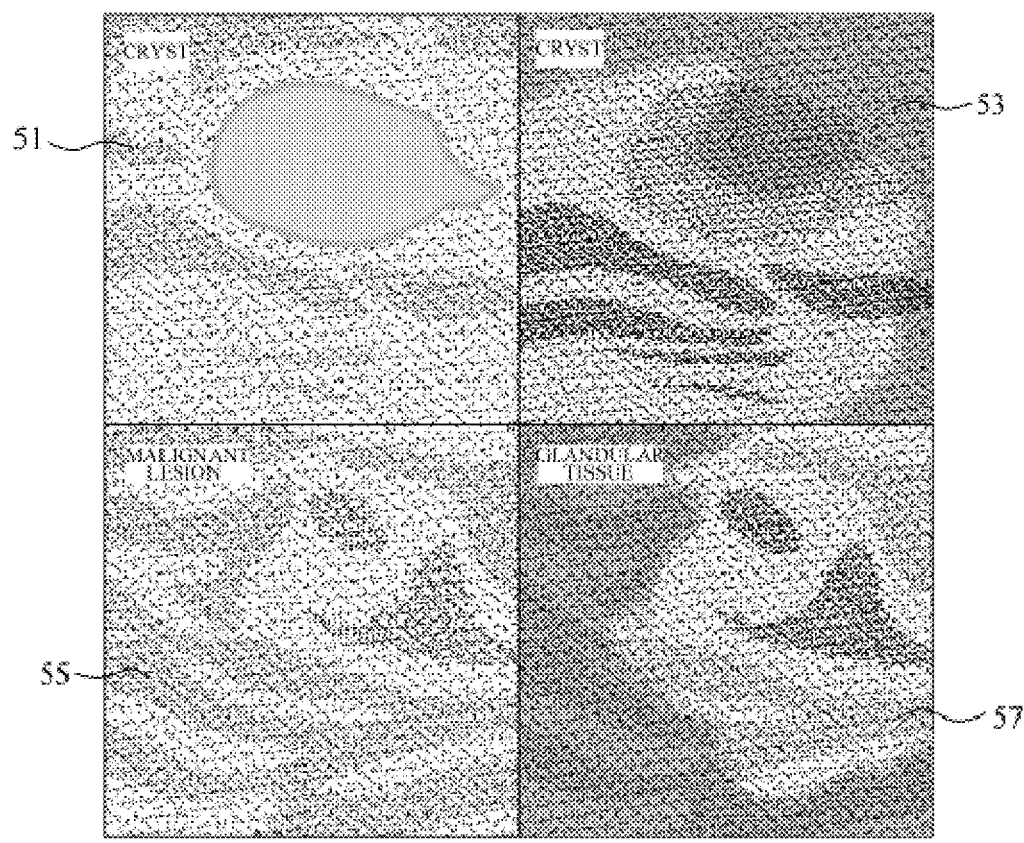
FIG. 5 is a diagram illustrating examples of a feature map extracted by the adjacent object detector shown in the example of FIG. 4.

FIG. 5 is a diagram illustrating examples of feature maps extracted by an example of the adjacent object detector illustrated in FIG. 4.

FIG. 5 demonstrates an example of a feature map group 50 that includes a cyst's feature map 51, a different cyst's feature map 54, a malignant lesions' feature map 55, and a glandular tissue's feature map 50. However, the feature map group 50 is merely an example, and it is obvious that other various feature maps may be further included to identify types and/or anatomical structures of more lesions. Such feature maps may be used similarly by the lesion candidate detector 33 illustrated in FIG. 3.

Figure 6:
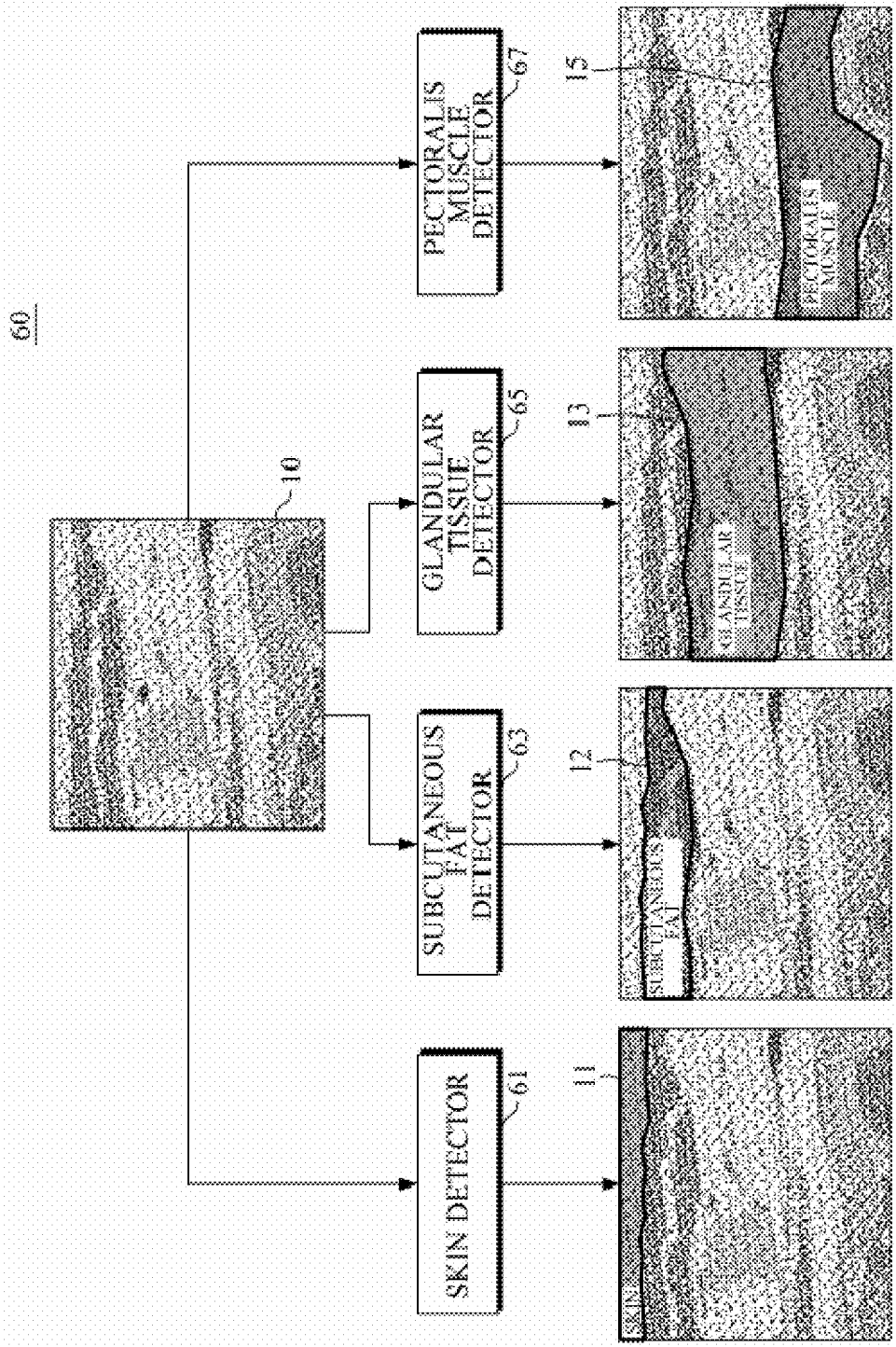
FIG. 6 is a diagram illustrating another example of operation of the adjacent object detector shown in the example of FIG. 3.

FIG. 6 is a diagram illustrating another example of an adjacent object detector shown in the apparatus illustrated in FIG. 3.

Referring to FIG. 6, a multi detector 60 including a plurality of individual object detectors 61, 63, 65, and 67 is provided as an example of the adjacent object detector 35 illustrated in FIG. 3. A skin object detector may detect only a skin region 11 from an original image 10. A subcutaneous fat detector 63 may detect only a subcutaneous fat region 12 from the original image 10. The glandular tissue detector 65 may detect only a glandular tissue region 13 from the original image 10. A pectoralis muscle detector 67 may detect a pectoralis muscle region from the original image 10. In the diagram illustrated in FIG. 6, the various detected anatomical objects or tissues are color-coded. For example, the portion of the image showing the skin, the subcutaneous fat, the glandular tissue and the pectoralis muscle, respectively, may be color-coded with blue, brown, green and tan highlights. The apparatus illustrated in FIG. 3 may allow such color-coded images to be displayed to a user on a display screen.

According to one example, each of a plurality of individual object detector 61, 63, 65 and 67 may use one of various deep learning techniques. For example, Deep Hierarchical Network (DHN), Convolutional Deep Belief Network (CDBN), or Deconvolutional Deep Network (DDN) may be used.

Figure 7:
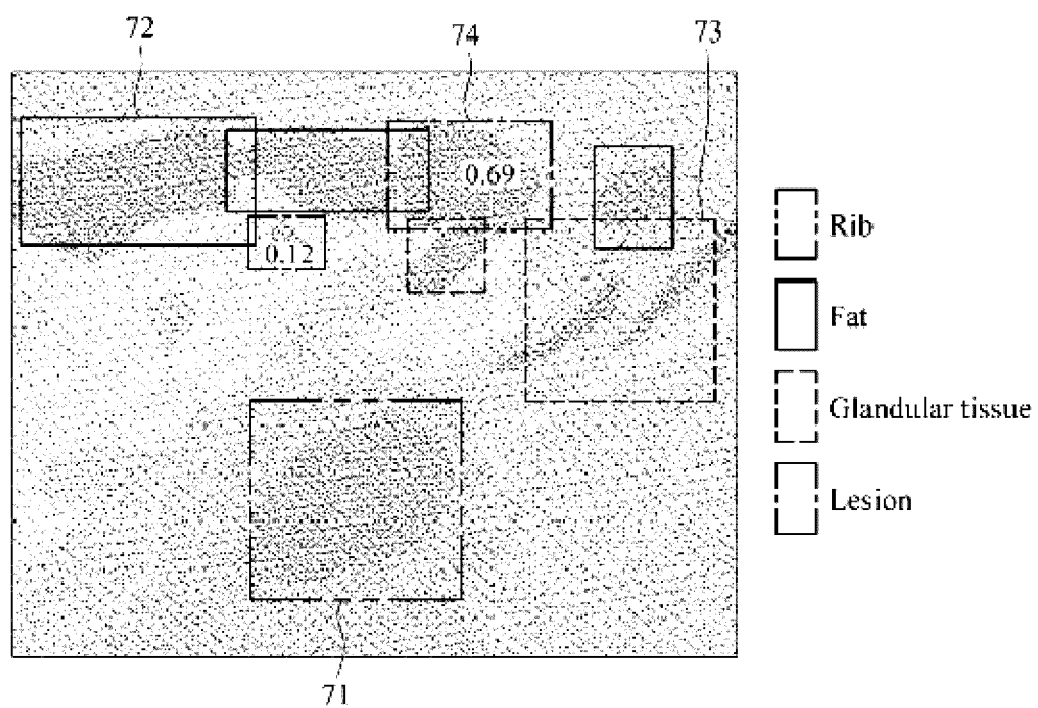
FIG. 7 is a diagram illustrating an example of a combined image in which lesion candidates and anatomical objects, detected from an original image shown in the embodiment of FIG. 3, are displayed.

FIG. 7 is a diagram illustrating an example of a combined image that indicates lesion candidates and anatomical objects detected from an original image illustrated in FIG. 3.

FIG. 7 is an example of a combined image that is output after the candidate remover 39 removes false positive lesion candidates from detected lesion candidates based on a verification result of the lesion candidate verifier 37. In this example, the image includes the remaining lesion candidates in an original image. As illustrated in FIG. 7, a rib region 71, a subcutaneous fat region 72, a glandular tissue region 73, and two lesion candidates are displayed in the original image. For example, the image may be output to a display screen or a touch screen of the display unit of the apparatus for lesion detection. In this example, a lesion candidate 74 is displayed with a confidence level of 69%, and the other lesion candidate is displayed with a confidence level of 0.12. Thus, the lesion candidate 74 is displayed with a visual indication for easy identification by the user. While, in this example, a rectangular box is used to indicate the lesion candidate 74, various other visual markings such as a contour line around the lesion or a color highlight may be used in another example.

Figure 8:
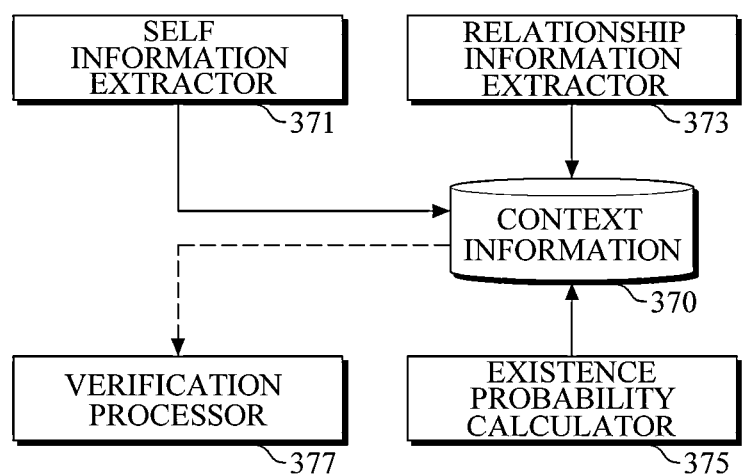
FIG. 8 is a block diagram illustrating an example of a lesion candidate verifier shown in the example of FIG. 3.

FIG. 8 is a block diagram illustrating in detail an embodiment of a lesion candidate verifier shown in the embodiment of FIG. 3.

Referring to FIG. 8, the lesion candidate verifier 37 in FIG. 3 may include components, such as a self information extractor 371, a relation information extractor 373, an existence probability calculator 373, a verification processor 377, and the like.

The self information extractor 371 may extract information on a lesion candidate itself detected by the lesion candidate detector 33 from the detected lesion candidate. The self information may include, for example, a confidence level score, values indicating brightness (or intensity of a pixel included in the lesion candidate), values indicating texture of the lesion candidate, and/or values indicating shape of the lesion candidate. Similarly, the self information extractor 371 may extract self information from an anatomical object detected by adjacent object detector 35. The self information of the anatomical object may include a confidence level score, values indicating brightness (or intensity) of pixels included in the anatomical object, values indicating texture of the anatomical object, and/or values indicating shape of the anatomical object. Self information extracted by the self information extractor 371 may be included in the context information 370.

The relationship information extractor 373 may include relationship information extracted from a correlation between each detected lesion candidate and each detected anatomical object. The relationship information may include a distance from each detected lesion candidate and each detected anatomical object, a location of each detected lesion candidate relative to each detected anatomical object, and/or information on similarities between each detected lesion candidate and each detected anatomical object in terms of brightness, texture, or shape. The relationship information extracted by the relationship information extractor 373 may be included in the context information 370.

The existence probability calculator 375 may calculate a probability distribution of the existence of a specific lesion candidate in a specific anatomical structure based on pre-established learning data. A probability distribution calculated by the existence probability calculator 375 may be included in the context information 370 as probability information.

The verification processor 377 is a component that performs a verifying function of the lesion candidate verifier 37 using information included in the context information 370. That is, the context information 370 may include self information obtained by the self information extractor 371, relationship information obtained by the relationship extractor 373, and/or probability information obtained by the existence probability calculator 375. As further described in the following with reference with FIG. 9, the context information 370 may include domain knowledge, self information, relationship information, probability information, and/or adjacent image information. The verification processor 377 may verify whether a specific lesion candidate is false positive based on the specific lesion candidate's domain knowledge, self information, relationship information, probability information, and/or adjacent image information, all of which are included in the context information 370.

The context information 370 may be a component included in the lesion candidate verifier 37 as a computer-readable storage medium to store context information including domain knowledge, self information, relationship information, probability information, and/or adjacent image information, or may be an external component placed outside of the lesion candidate verifier 37 to transmit/receive data through wired/wireless communication connection to the lesion candidate verifier 37. Hereinafter, context information included in the context information 370 is described in detail with reference to FIG. 9.

Figure 9:
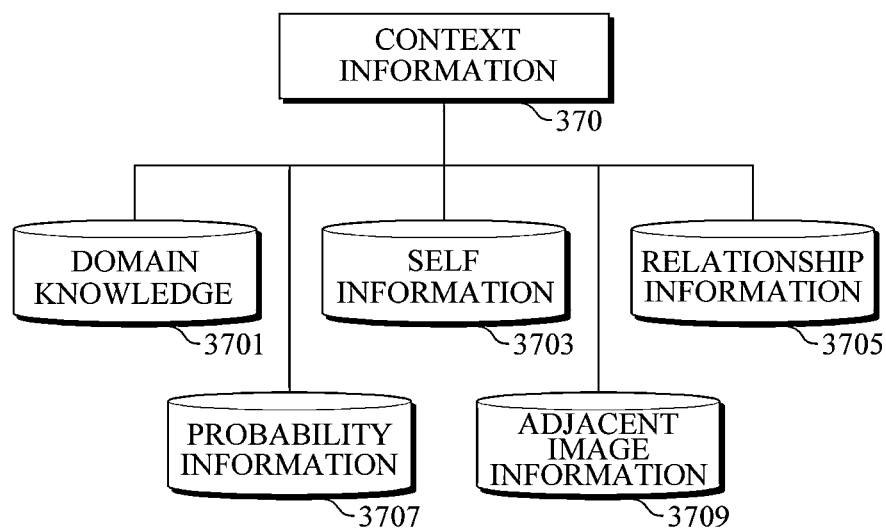
FIG. 9 is a block diagram illustrating an example of context information that is used by the lesion candidate verifier shown in the example of FIG. 3.

FIG. 9 is a block diagram illustrating an example of context information used by a lesion candidate verifier shown in FIG. 3.

Referring to FIG. 9, anatomical context information stored in the context information 370 may include domain knowledge 3701, self information 3703, relationship information 3705, probability information 3707, and/or adjacent image information 3709.

The domain knowledge 3701 is information that indicates a location relationship in each region. The domain knowledge 3701 may include at least general information about an anatomical object such as, for example, "a specific part of a human body includes predetermined anatomical objects", "different anatomical objects have a predefined location relationship in a specific part of a human body" and "identical anatomical objects are gathered."

For example, in the case of an ultrasound breast image, domain knowledge may include anatomical location information. For instance, domain knowledge may include anatomical location information like "a breast includes skin, subcutaneous fat, glandular tissue, retromammary fat, pectoralis muscle, and a rib as anatomical objects" or "a breast includes skin placed there atop, and then, subcutaneous fat, glandular tissue, retromammary fat, pectoralis muscle, and a rib placed below skin in the order named.

In addition, the domain knowledge 3701 may include domain knowledge associated with a lesion candidate, for example, "a specific lesion candidate exists only between specific anatomical objects in a specific part of a human body."

For an ultrasound breast image, the domain knowledge 3701 may include general medical location information, for example, "a cyst of breast cancer exists in a glandular tissue region at a time when the breast cancer is palpable."

In addition, the context information 370 may include self information 3703, which is extracted from each detected lesion candidate and each detected anatomical object. The self information 3703 may include confidence level information, brightness information, texture information and/or shape information of each lesion candidate/anatomical object. For example, the self information 3703 may include a value of brightness of each pixel, a value of texture, and information on a shape of a specific lesion candidate/anatomical object.

In addition, the context information 370 may include the relationship information 3705 that is extracted from a correlation between each detected lesion candidate and each detected anatomical object. The relationship information 3705 may include at least one of a distance between each lesion and each anatomical object, a location of a lesion candidate relative to each anatomical object, and information on similarity between each lesion candidate and each anatomical object in terms of brightness, texture or shape. Herein, a location of a lesion candidate relative to each anatomical object may be relationship information about whether the lesion candidate is located below skin and subcutaneous fat but above pectoralis muscle in a breast image.

Moreover, the context information 370 may include the probability information 3707. The probability information 3707 may be acquired from pre-established learning data. The probability information 3707 may be a probability distribution of the existence of a lesion candidate or anatomical object in a specific medical image.

For example, in an example in which an ultrasound breast image is used as the medical image, the probability information 3705 may include a probability distribution, for example, "skin exists on the top of the image at 100%", "subcutaneous fat may be found 10 cm away from the top of the image at 50%", and "a lesion such as a cyst of breast cancer may be found between subcutaneous fat and retromammary fat at 10 to 31%."

Furthermore, the context information 370 may include adjacent image information 3709. In the case where a medical image is one of 2D continuous frames or one of 3D cross-sectional images, the adjacent image information 3709 may include location information of a lesion candidate or an anatomical object that is obtained from an adjacent frame/cross-section.

For example, in the case where the current medical image is one of slices of a 3D ultrasound volume image, information on a lesion detected from previous adjacent slices and/or location information of an anatomical object detected from previous adjacent slices is highly associated with a lesion and/or anatomical object detected from the current slice. Thus, a previously detected anatomical object's location information included in adjacent image information may be used as useful reference in verifying and adjusting a lesion candidate and/or an anatomical object detected from the current image.

Figure 10:
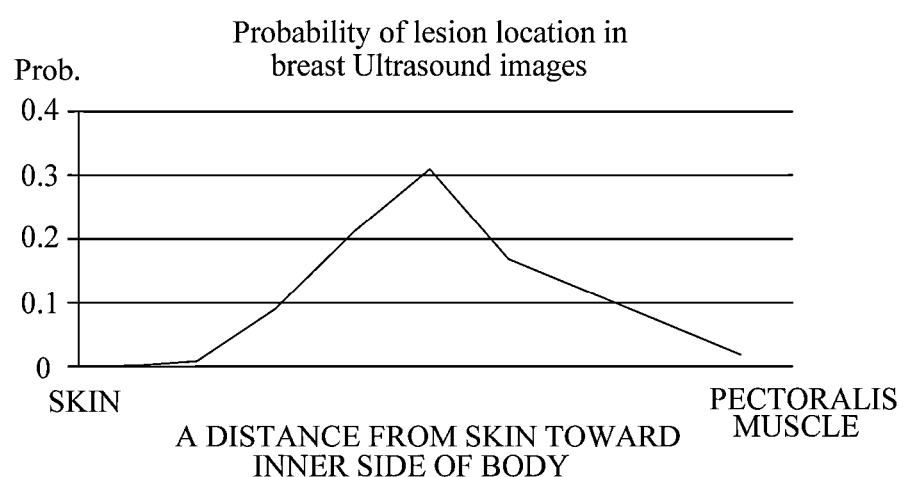
FIG. 10 is a graph illustrating an example of probability information as an example of context information.

FIG. 10 is a graph illustrating an example of probability information as an example of context information described in FIG. 9.

FIG. 10 illustrates a graph showing a probability of a lesion to be discovered in a specific region of an ultrasound breast image. In the graph, a horizontal axis represents a distance from skin to pectoralis muscle, and a vertical axis represents a probability of a lesion to be discovered. The graph shows that a lesion is less likely to exist in a region close to skin and pectoralis muscle, and that a lesion may be discovered at an intermediate location between skin and pectoralis muscle at 31%. The probability distribution may be acquired from learning data pre-established based on data that has been accumulated in the process of lesion detection. The location information regarding a lesion candidate may be used to determine whether the lesion candidate is more or less likely to be a false positive lesion candidate.

Figure 11:
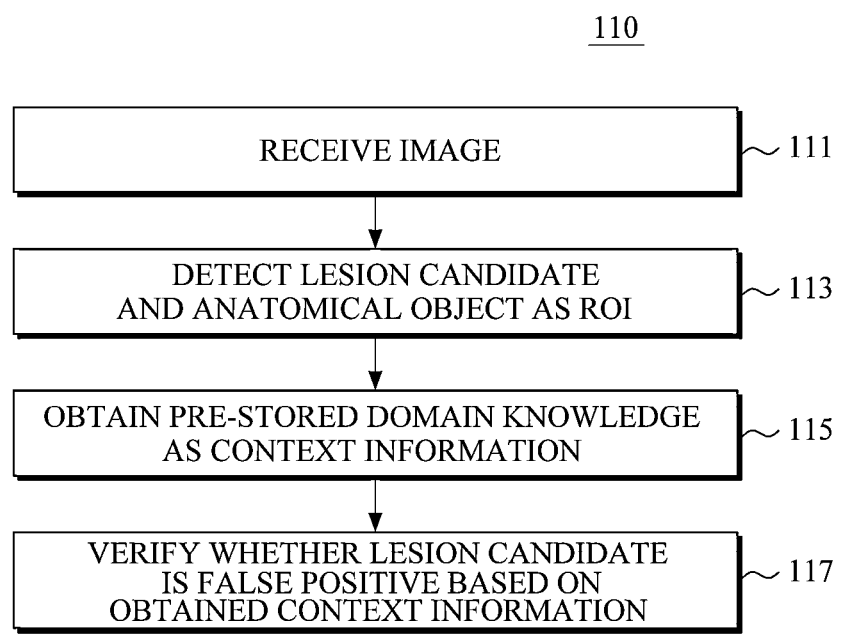
FIG. 11 is a flow chart illustrating an example of a method for removing one or more false-positive lesion candidates from a medical image.

FIG. 11 is a flow chart illustrating an example of a method for detecting lesion by removing a false positive lesion candidate from a medical image.

Referring to FIG. 11, a method 110 for detecting lesion by removing a false positive lesion candidate from a medical image may involve the acquisition of a medical image. For example, a medical image may be received by an image receiver of the apparatus shown in FIG. 3 in operation 111. The medical image may be received from a medical image diagnostic/capturing device that captures a specific part of a human body using ultrasound waves or X-rays, or from a storage device that stores medical images captured by the medical image diagnostic/capturing device.

Once the image is received, the received image is analyzed, and then, the lesion candidate detector 33 and the adjacent object detector 35 in the apparatus shown in FIG. 3 detect a lesion candidate and an anatomical object located in specific regions of the received image as Regions of Interest (ROIs) in operation 113. During operation 113, if the received image is an ultrasound breast image, a region suspected of being a lesion, such as a cyst of breast cancer, is detected as a lesion candidate, and then skin, fat, glandular tissue, muscle and bones are detected as anatomical objects.

Then, in operation 115, context information is obtained from a computer-readable storage medium, for example, by the lesion candidate verifier 37 shown in FIG. 3, to be used as information when determining whether a lesion candidate is false positive. The context information may be the context information 370 shown in FIG. 3. In this example, the context information 370 may include domain knowledge, and may be pre-stored in a computer readable storage medium. The domain knowledge may include domain knowledge about the lesion candidate and/or domain knowledge about an anatomical object. In addition, the domain knowledge may be the domain knowledge 3701 shown in FIG. 9.

Once the context information is obtained, the lesion candidate verifier 37 may verify based on the obtained context information whether a lesion candidate amongst all the ROIs is false positive in operation 117. For example, if a lesion candidate is determined to exist in a skin region, the lesion candidate is less likely to be determined as being a true positive lesion, and thus, may be determined to be false positive. Alternatively, if a lesion candidate is determined to exist in a glandular tissue region, the lesion candidate is highly likely to be determined to be a true lesion, and thus, may be determined to be not false positive.

The verification result obtained during operation 117 is used, for example, by the candidate remover 39 shown in FIG. 3, to thereby output a result of lesion candidates from which any false positive lesion candidate is removed.

Figure 12:
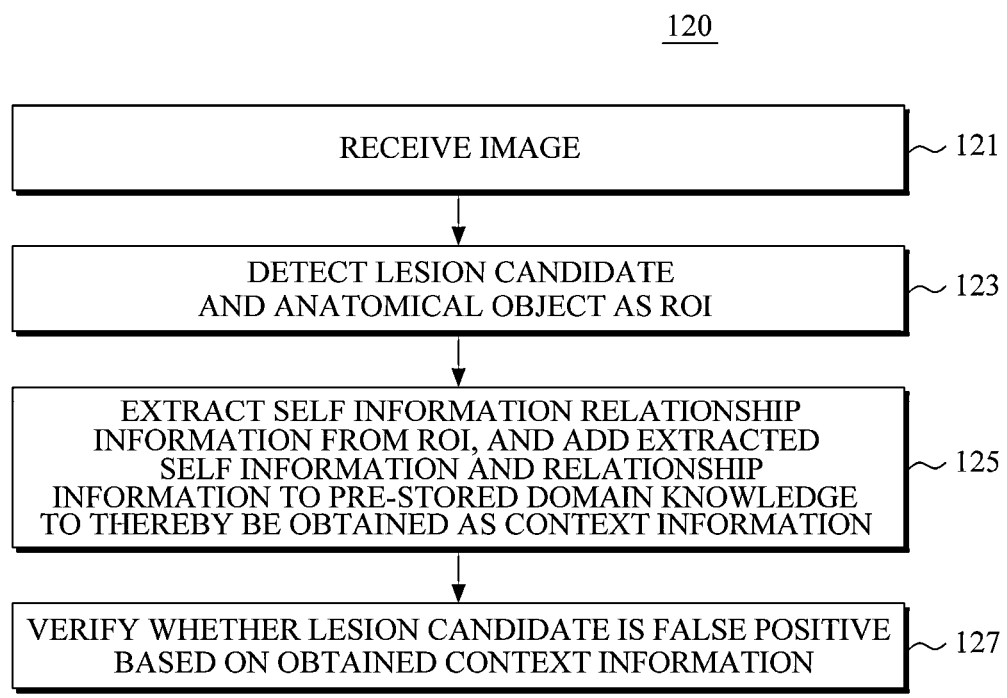
FIG. 12 is a flow chart illustrating another example of a method for removing one or more false-positive lesion candidates from a medical image.

FIG. 12 is a flow chart illustrating another example of a method for removing a false positive lesion candidate from a medical image.

Referring to FIG. 12, a method 120 for detecting lesion by removing a false positive lesion candidate from a medical image may involve, for example, obtaining a medical image by the image receiver illustrated in FIG. 3, in operation 121. The medical image may be received from a medical image diagnostic/capturing device that captures a specific part of a human body using ultrasound waves or X-rays, or from a storage device that stores medical images captured by the medical image diagnostic/capturing device.

Once the image is received, the lesion candidate detector 33 and the adjacent object detector 35 of the apparatus shown in FIG. 3 analyze the received image and detect a lesion candidate and an anatomical object in specific regions of the received image as Regions of Interest (ROIs), in operation 123. The analysis may be performed by a computer processor. During operation 123, if the image is an ultrasound breast image, a region suspected of being a lesion, such as a cyst of breast cancer, may be detected, and skin, fat, glandular tissue, muscle, and bones may be detected as anatomical objects.

Then, in operation 125, context information is acquired, for example, by the lesion candidate verifier 37 from a computer-readable storage medium, to be used as resources when determining whether a specific lesion candidate amongst the detected regions is false positive. The context information may be the context information 370 shown in FIG. 3. In this example, the context information 370 may include domain knowledge, and may be stored in a computer readable medium. The domain knowledge may include domain knowledge of a lesion candidate and/or domain knowledge of an anatomical object. The domain knowledge may be the domain knowledge 3701 illustrated in FIG. 9.

In addition, during operation 125, the lesion candidate verifier 37 may extract self information and relationship information from each ROI detected in operation 123. The extracted self information may include information of a confidence level, brightness, texture, and/or shape of a corresponding ROI which may be a lesion candidate or an anatomical object. For example, extracted self information may include a value of brightness of a pixel composing a specific lesion candidate/anatomical object, a value of texture of the specific lesion candidate/anatomical object, and information on a shape of the specific lesion candidate/anatomical object. In addition, extracted relationship information may include a distance between a lesion candidate and an anatomical object, a location of the lesion candidate relative to the anatomical object, or information on similarity between the lesion candidate and the anatomical object in terms of brightness, texture, or shape. The extracted self information and relationship information may be added to the context information 370 as the self information 3703 and the relationship information 3705, respectively, which are shown in FIG. 9.

Once context information of a specific lesion candidate is acquired, whether the specific lesion candidate among ROIs is false positive is verified, for example, by the lesion candidate verifier 37 shown in FIG. 3, based on the acquired context information, that is, self information, relationship information and domain knowledge of the specific lesion candidate in operation 127. For example, if a lesion candidate is determined to exist in a skin region, the lesion candidate is determined less likely to be a true lesion, and thus, the lesion candidate may be determined to be false positive. In another example, if a lesion candidate is determined to exist in a glandular tissue region, the lesion candidate is determined highly likely to be a true lesion, and thus, may be determined to be not false positive.

The verification result obtained during operation 127 may be used, for example, by the candidate remover 39 shown in FIG. 3, to thereby output a result of lesion candidates from which any false positive lesion candidate is removed.

Figure 13:
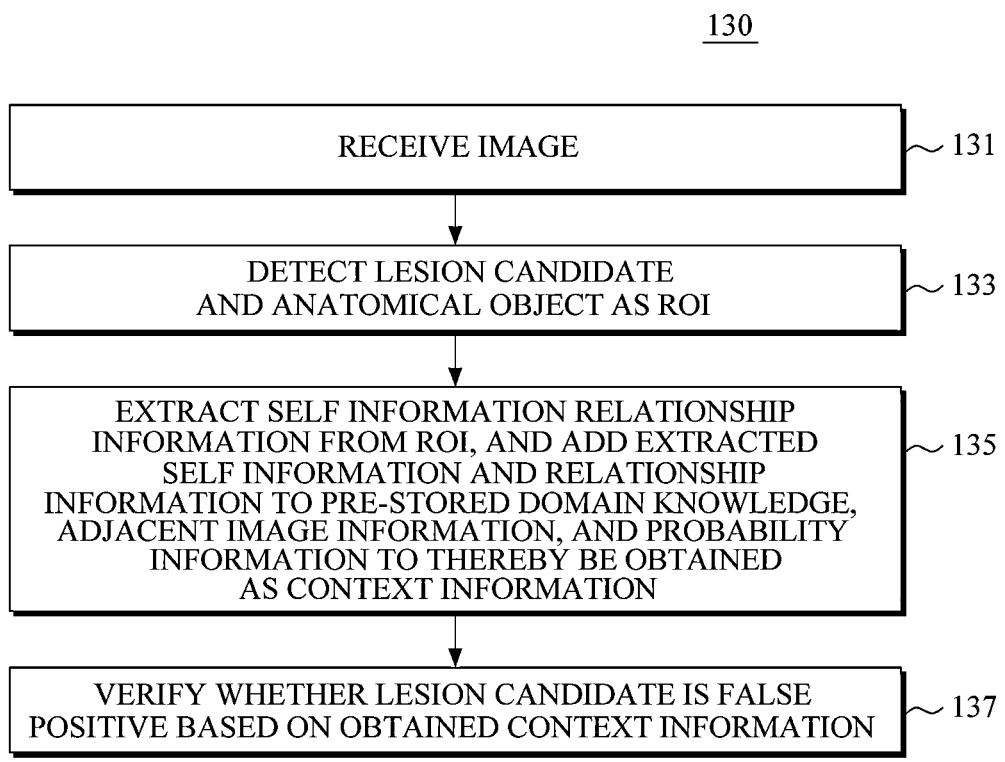
FIG. 13 is a flow chart illustrating another example of a method for removing one or more false-positive lesion candidates from a medical image.

FIG. 13 is a flow chart illustrating another example of a method for removing a false positive lesion candidate in a medical image. FIG. 13 is described with references to the apparatus illustrated in FIG. 3.

Referring to FIG. 13, a method 130 for detecting a lesion by removing a false positive lesion candidate in a medical image may involve, for example, obtaining a medical image by an image receiver of the apparatus illustrated in FIG. 3, in operation 131. The medical image may be received from a medical image diagnostic/capturing device that captures a specific part of a human body using ultrasound waves or X-rays, or from a storage device that stores medical images captured by the medical image diagnostic/capturing device. The storage device and the medical image diagnostic/capturing device may be collectively referred to as a medical imagining apparatus.

Once the medical image is received, the received medical image is analyzed, and then, the lesion candidate verifier 33 and the adjacent object detector 35 in the apparatus illustrated in FIG. 3 detects a lesion candidate and an anatomical object, respectively, from the analyzed medical image as an ROI in operation 133. During operation 133, if the medical image is an ultrasound breast image, a region suspected of being a lesion, such as a breast cancer cyst, may be detected as a lesion candidate, and skin, fat, glandular tissue, muscle, and bones may be detected as being anatomical objects.

Then, in operation 135, context information is obtained, for example, by the lesion candidate verifier 37 in FIG. 3 from a computer-readable storage medium, to be used as resources when determining whether a specific lesion candidate among the detected ROIs is false positive. The context information may include the context information 370 in FIG. 3. In this example, the context information 370 may include domain knowledge, and may be stored in a computer-readable storage medium. The domain knowledge may include domain knowledge of a lesion candidate and domain knowledge of an anatomical object. The domain knowledge may be the domain knowledge 3701 in FIG. 9.

In addition, during operation 135, the lesion candidate verifier may extract self information and relationship information from each detected ROI. The extracted self information may include confidence level information, brightness information, texture information, and/or shape information of an ROI, that is, a lesion candidate or an anatomical object. For example, self information may include a confidence level of a specific lesion candidate/anatomical object, a value indicating brightness of the specific lesion candidate/anatomical object, a value indicating texture of the specific lesion candidate/anatomical object, and information on shape of the specific lesion candidate/anatomical object. In addition, relationship information may include a distance between a lesion candidate between a lesion and an anatomical object, a location of the lesion relative to the anatomical object (e.g. a lesion candidate in a breast image may be positioned below skin and subcutaneous fat, but above pectoralis muscle), and information on similarity between the lesion candidate and the anatomical object in terms of brightness, texture or shape. The extracted self information and relationship information may be added to the context information 370 as the self information 3703 and the relation information 3705, respectively, which are shown in FIG. 9.

In addition, the context information may include probability information. The probability information may be acquired from pre-established learning data. The probability information may be a probability distribution of the existence of a lesion candidate/anatomical object in a specific medical image. Just like the domain knowledge, the probability information is also pre-stored. The probability information may be added to the context information 370 as the probability information 3703 shown in FIG. 9.

Moreover, the context information may include adjacent image information. If the medical information is one of 2D continuous frames or one of 3D cross-sectional images, the adjacent image information may be acquired from a frame/cross-section which is adjacent to the current frame/cross-section. The adjacent image information may include location information of a lesion or an anatomical object. Just like the domain knowledge and probability information, the adjacent image information is pre-stored. For example, the adjacent image information may be added to the context information 370 as the adjacent image information 3709 shown in FIG. 9.

Once context information of a specific lesion candidate is acquired, operation 137 may be performed, for example, by the lesion candidate verifier 37 shown in FIG. 3, based on the context information, that is, the self information, relation information, and domain knowledge of the specific lesion candidate to verify whether the specific lesion candidate amongst ROIs is false positive. For example, if a lesion candidate is determined to exist in a glandular tissue region, the lesion candidate is determined highly likely to be a true lesion, and thus, the lesion candidate may be determined to be not false positive.

The verification result obtained in operation 137 is used, for example, by the candidate remover shown in FIG. 3, to output a result of lesion candidates from which any false positive lesion candidate is removed.

The above-described apparatus for removing a false positive lesion candidate from a medical image may be executed by a computing device that includes at least some of a processor, a memory, a user input device and a presentation device. The memory is a medium that stores computer-readable software, an application, a program module, a routine, an instruction and/or data, which are encoded and set to perform a specific task once executed by a processor. The processor may read and implement computer-readable software, an application, a program module, a routine, an instruction, and/or data, which are stored in a memory. The user input device may be a means that enables a user to input an instruction requiring a processor to execute a specific task or input data necessary for the specific task. The user input device may include a physical/virtual keyboard or keypad, key buttons, a mouse, a joystick, a trackball, a touch-sensitive input device, and a microphone. The presentation device may include a display, a printer, a speaker, and a vibration device.

The computing device may include a smartphone, a tablet, a laptop, a desktop, a server, a client, and other various devices. The computing device may be a single stand-alone device or a plurality of computing devices that operate in a distributive environment in which a plurality of computing devices cooperates via a communication network.

In addition, the above-described method for removing a false positive lesion candidate from a medical image may be implemented by a computing device that includes a processor and a memory, wherein the memory stores computer readable software, an application, a program module, a routine, an instruction, and/or a data structure that is encoded to implement the above-described method.

The examples of apparatuses for removing a false positive lesion candidate from a medical image, which are described above with reference to FIGS. 1 to 10, are merely exemplary. It is readily apparent for those skilled in the art that different apparatuses having various configurations are possible within the scope of the following claims. Each component in an apparatus for removing a false positive lesion candidate from a medical image may be implemented by hardware that includes a circuit for a function of its own. In addition, each component in an apparatus for removing a false positive lesion candidate from a medical image may be implemented by a combination of computer-readable software, firmware, and hardware, such that each component executes a specific task once implemented by a processor of a computing device.

In addition, the methods for removing a false positive lesion candidate, which are described above with reference to FIGS. 11 to 13, are merely exemplary. Modifications to the embodiments will be readily apparent for those skilled in the art that within the scope of the following claims. The examples of the methods for removing one or more false positive lesion candidates may be encoded as a computer-executable instruction to execute a specific task once implemented by a processor of a computer device. The computer-executable instruction may be encoded by a software developer into a program language and then into a machine language.

The methods and/or operations described above may be recorded, stored, or fixed in one or more non-transitory computer-readable storage media that includes program instructions to be implemented by a computer to cause a processor to execute or perform the program instructions. The media may also include, alone or in combination with the program instructions, data files, data structures, and the like. Examples of non-transitory computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

The display may be implemented as a liquid crystal display (LCD), a light-emitting diode (LED) display, a plasma display panel (PDP), a screen, a terminal, and the like. A screen may be a physical structure that includes one or more hardware components that provide the ability to render a user interface and/or receive user input. The screen can encompass any combination of display region, gesture capture region, a touch sensitive display, and/or a configurable area. The screen can be embedded in the hardware or may be an external peripheral device that may be attached and detached from the apparatus. The display may be a single-screen or a multi-screen display. A single physical screen can include multiple displays that are managed as separate logical displays permitting different content to be displayed on separate displays although part of the same physical screen.

A user interface may be responsible for inputting and outputting input information regarding an image or an input from a user. The user interface may further include an input/output device such as, for example, a mouse, a keyboard, a touch screen, a monitor, a speaker, a screen, and a software module for running the input/output device.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for lesion detection, the apparatus comprising a processor configured to:
    detect lesion candidates from a medical image;
    detect anatomical objects from the medical image by extracting at least one feature map from the medical image and comparing the at least one feature map to at least one pre-stored feature map;
    verify each of the lesion candidates based on anatomical context information comprising first information regarding a location relationship between each of the lesion candidates and the anatomical objects and second information regarding a probability distribution of a lesion for each of locations of the medical image, the probability distribution being obtained from a learning data established prior to detecting the lesion candidates; and
    determine at least one true positive lesion by removing one or more false positive lesion candidate from among the detected lesion candidates based on a verification result of the lesion candidate verifier.

2. The apparatus of claim 1, further comprising:
    an image receiver configured to obtain the medical image, wherein the medical image is an image of a human breast captured using ultrasound waves or X-rays;
    wherein the processor is further configured to detect at least one of skin, fat, glandular tissue, muscle, and bone from the breast image as an anatomical object; and
    wherein the processor is further configured to verify each of the lesion candidates based on anatomical context information comprising information regarding a location relationship between each of the lesion candidates and the at least one of skin, fat, glandular tissue, muscle, and bone.

3. The apparatus of claim 1, wherein the processor is further configured to detect the lesion candidates from the medical image using at least one of Haar feature detection technique, deformable part model (DPM), and deep learning technique.

4. The apparatus of claim 1, wherein the processor is further configured to detect the anatomical objects individually from the medical image.

5. The apparatus of claim 4, wherein processor is further configured to use deep learning technique, sliding window technique, or superpixel technique.

6. The apparatus of claim 1, wherein the processor is further configured to simultaneously detect the anatomical objects from the medical image.

7. The apparatus of claim 6, wherein the processor is further configured to use deep learning technique, sliding window technique, or superpixel technique.

8. The apparatus of claim 6, wherein the processor is further configured to: extract a plurality of feature maps from the whole medical image or a part of the medical image, allocate the extracted feature maps with corresponding anatomical objects, and label a location of a feature map allocated with a specific anatomical object in the medical image as the specific anatomical object.

9. The apparatus of claim 1, wherein the processor is further configured to use at least one of Support Vector Machine (SVM), Artificial Neural Network (ANN), deep learning technique, and Bayesian Network.

10. The apparatus of claim 1, wherein the anatomical context information comprises domain knowledge of the anatomical objects and domain knowledge of the lesion candidates, the domain knowledge of the anatomical objects comprising at least one of: "a specific part of a human body has predefined anatomical objects", "different anatomical objects have a predefined location relationship in a specific part of a human body" and "the identical anatomical objects are gathered", and wherein the domain knowledge of the lesion candidate comprising "a specific lesion candidate exists only in specific anatomical objects of a specific part of a human body".

11. The apparatus of claim 10, wherein the anatomical context information comprises self information that is extracted from the detected lesion candidate and the detected anatomical object, and the self information comprises at least one of confidence level information, brightness information, texture information, and shape information.

12. The apparatus of claim 10, wherein the anatomical context information comprises relationship information that is extracted from a correlation between each of the lesion candidates and each of the anatomical object; and
    wherein the relationship information comprises at least one of a distance between each of the lesion candidates and each of the anatomical objects, a location of each of the lesion candidates relative to each of the anatomical objects, and information on similarity between each of the lesion candidates and each of the anatomical objects in terms of brightness, texture, or shape.

13. The apparatus of claim 10, wherein, in response to the medical image being one of 2D continuous frames or one of 3D cross-sectional images, the anatomical context information further comprises adjacent image information obtained from an adjacent frame or cross-section, which comprises location information of each of the lesion candidates and each of the anatomical objects.

14. The apparatus of claim 1, further comprising a display screen configured to display the at least one true positive lesion with information regarding a confidence level for each of the lesion candidates.

15. A method of lesion detection, the method comprising:
    detecting, using a processor, lesion candidates from a medical image;
    detecting, using the processor, anatomical objects from the medical image by extracting at least one feature map from the medical image and comparing the at least one feature map to at least one pre-stored feature map;
    verifying, using the processor, each of the lesion candidate based on anatomical context information comprising first information regarding a location relationship between the lesion candidates and the anatomical objects and second information regarding a probability distribution of a lesion for each of locations of the medical image, the probability distribution being obtained from a learning data established prior to detecting the lesion candidates; and
    determining at least one true positive lesion by removing, using the processor, one or more false positive lesion candidates from the detected lesion candidates based on a verification result.

16. The method of claim 15, further comprising:
    obtaining the medical image from a medical imaging apparatus,
    wherein the medical image is an image of a breast of a human body captured using ultrasound waves or X-rays;
    wherein the detecting of anatomical objects comprises detecting at least one of skin, fat, glandular tissue, muscle, and bone from the breast image as an anatomical object; and wherein the verifying of each of the lesion candidates comprises verifying each of the lesion candidates based on anatomical context information comprising information regarding a location relationship between the lesion candidates and the at least one of skin, fat, glandular tissue, muscle, and bone.

17. The method of claim 15, wherein the detecting of the anatomical objects comprises detecting a plurality of individual objects to detect the anatomical objects from the medical image individually.

18. The method of claim 15, wherein the detecting of the anatomical objects comprises detecting all of the anatomical objects from the medical image simultaneously.

19. The method of claim 18, wherein the simultaneous detecting of all of the anatomical objects comprises:
    extracting a plurality of feature maps from the whole medical image or a part of the medical image,
    allocating each of the plurality of extracted feature maps with corresponding anatomical objects, and
    labeling a location of a feature map allocated with a specific anatomical object in the medical image with the specific anatomical object.

20. The method of claim 15, wherein the verifying of each of the lesion candidates utilizes at least one of Support Vector Machine (SVM), Artificial Neural Network (ANN) and Bayesian Network.

21. The method of claim 15,
    wherein the anatomical context information comprises domain knowledge of the anatomical objects and domain knowledge of the lesion candidates; and
    wherein the domain knowledge of the anatomical objects comprises at least one of: "a specific part of a human body has predefined anatomical objects", "different anatomical objects have a predefined location relationship in a specific part of a human body" and "the identical anatomical objects are gathered", and the domain knowledge of the lesion candidate comprises "a specific lesion candidate exists only in specific anatomical objects of a specific part of a human body".

22. The method of claim 21,
    wherein the anatomical context information comprises self information that is respectively extracted from the lesion candidates and the anatomical objects; and
    wherein the self information comprises at least one of confidence level information, brightness information, texture information, and shape information.

23. The method of claim 21,
    wherein the anatomical context information comprises relationship information that is extracted from a correlation between each of the lesion candidates and each of the anatomical objects; and
    wherein the relationship information comprises at least one of a distance between each of the lesion candidates and each of the anatomical objects, a location of each of the lesion candidates relative to each of the anatomical objects, and information on similarity between each of the lesion candidates and each of the anatomical objects in terms of brightness, texture, or shape.

24. The method of claim 21, wherein, in response to the medical image being one of two-dimensional (2D) continuous frames or one of three-dimensional (3D) cross-sectional image, the anatomical context information further comprises adjacent image information from an adjacent frame or an adjacent cross-section, which comprises location information of each of the lesion candidates or each of the anatomical objects.

25. The method of claim 15, further comprising displaying the at least one true positive lesion with information regarding a confidence level for each of the lesion candidates.

26. An apparatus for lesion detection, the apparatus comprising:
    a memory configured to store a medical image; and
    a processor configured to:
        detect lesion candidates and anatomical objects from the medical image, verify each of the detected lesion candidates based on anatomical context information comprising first information regarding a location relationship between each of the lesion candidates and the detected anatomical objects and second information regarding a probability distribution of a lesion for each of locations of the medical image, the probability distribution being obtained from a learning data established prior to detecting the lesion candidates, and
        determine at least one true positive lesion by removing one or more false positive lesion candidates from among the detected lesion candidates based on a verification result, the detecting of the anatomical objects including extracting at least one feature map from the medical image and comparing the at least one feature map to at least one pre-stored feature map.

27. The apparatus of claim 26, further comprising:
    an image receiver configured to:
        obtain the medical image from a medical imaging apparatus, and
        store the medical image in the memory, the medical image being an image of a human breast captured using ultrasound waves or X-rays, and the anatomical objects comprising at least one of skin, fat, glandular tissue, muscle, and bone from the breast image; and
    a display screen configured to output a view of the medical image in which the lesion candidates remaining after the removing of the one or more false positive lesion candidates are displayed.

* * * * *